US006793919B2

(12) United States Patent
Mohler

(10) Patent No.: US 6,793,919 B2
(45) Date of Patent: Sep. 21, 2004

(54) METHODS FOR TREATING RHEUMATOID ARTHRITIS USING IL-17 ANTAGONISTS

(75) Inventor: Kendall M. Mohler, Poulsbo, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 10/033,522

(22) Filed: Oct. 18, 2001

(65) Prior Publication Data

US 2002/0136724 A1 Sep. 26, 2002

Related U.S. Application Data

(60) Provisional application No. 60/241,230, filed on Oct. 18, 2000.

(51) Int. Cl.⁷ ...................... A61K 39/395; A61K 45/00; C07K 14/00; C07K 16/00

(52) U.S. Cl. ............................... 424/143.1; 424/139.1; 424/85.2; 530/351; 530/388.1; 530/389.1; 530/388.22

(58) Field of Search ........................... 424/143.1, 139.1, 424/852; 530/351, 388.1, 389.1, 388.22

(56) References Cited

U.S. PATENT DOCUMENTS

| | | | |
|---|---|---|---|
| 5,869,286 A | 2/1999 | Yao et al. | |
| 6,072,033 A | 6/2000 | Yao et al. | |
| 6,072,037 A * | 6/2000 | Yao et al. ............... | 530/388.22 |
| 6,083,906 A | 7/2000 | Troutt | |
| 6,096,305 A | 8/2000 | Yao et al. | |
| 6,100,235 A | 8/2000 | Yao et al. | |
| 6,191,104 B1 | 2/2001 | Spriggs et al. | |
| 6,197,525 B1 | 3/2001 | Yao et al. | |
| 6,680,057 B1 | 1/2004 | Yao et al. | |

FOREIGN PATENT DOCUMENTS

| | | |
|---|---|---|
| WO | WO 95/18826 | 7/1995 |
| WO | WO 96/29408 | 9/1996 |
| WO | WO 97/04097 | 2/1997 |
| WO | WO 98/23284 | 6/1998 |
| WO | WO 99/14240 | 3/1999 |
| WO | WO 99/60127 | 11/1999 |
| WO | WO 00/15759 | 3/2000 |
| WO | WO 00/55204 | 9/2000 |
| WO | WO 01/68705 | 9/2001 |
| WO | WO 01/68859 | 9/2001 |

OTHER PUBLICATIONS

Chabaued, M. et al. Arthritis and Rheumatism, 1999, vol. 42, No. 5, pp. 963–970.*
Arend, W. et al. Arthritis and Rheumatism, 1995, vol. 38, No. 2, pp. 151–160.*
Aarvak et al., "Analysis of IL–17 and other cytokines and surface markers of RA inflammatory T cell clones," *American College of Rheumatology (ACR) meeting*, Poster 1448, Nov. 1997.

Amin, A. R. et al., "The expression and regulation of nitric oxide synthase in human osteoarthritis–affected chondrocytes: Evidence for up–regulated neuronal nitric oxide synthase," *J. Exp. Med.*, 182:2097–2102, Dec. 1995.
Antonysamy, M. et al., "Evidence for a of role IL–17 in organ allograft rejection: IL–17 promotes the functional differentiation of dendritic cell progenitors," *J. Immunol.*, 162:577–584, 1999.
Attur, M. G. et al., "Interleukin–17 up–regulation of nitric oxide production in human osteoarthritis cartilage," *Arthritis & Rheumatism*, 40(6):1050–1053, 1997.
Baragi, V. M. et al., "Transplantation of transduced chondrocytes protects articular cartilage from interleukin 1–induced extracellular matrix degradation," *J. Clin. Invest.*, 96(5):2454–2460, 1995.
Caron, J. P. et al., "Chondroprotective effect of intraarticular injections of interleukin–1 receptor antagonist in experimental osteoarthritis," *Arthritis & Rheum.*, 39(9):1535–1544, 1996.
Chabaud, M. et al., "Regulation of the effects of IL 17 on IL 6 and LIF production by RA synoviocytes," *American College of Rheumatology (ACR) meeting*, Poster 1449, Nov. 1997.
Chabaud, M. et al., "Human Interluekin–17: A T Cell–Derived Proinflammatory Cytokine Produced by the Rheumatoid Synovium," *Arthritis & Rheumatism*, 42(5):963–970, 1999.
Chabaud, M. et al., "Contribution of interleukin 17 to synovium matrix destruction in rheumatoid arthritis," *Cytokine*, 12(7):1092–1099, 2000.
Chabaud, M. et al., "Enhancing effect of IL–17 on IL–1–Induced IL–6 and leukemia inhibitory factor production by rheumatoid arthritis synoviocytes and its regulation by TH2 cytokines," *J. Immunol.*, 161:409–414, 1998.
Dudler et al., "In vivo effects of murine recombinant interleukiN–17 on synovial joint in mice," *American College of Rheumatology (ACR) meeting*, Poster 1450, Nov. 1997.
Fossiez et al., "T cell interleukin–17 induces stromal cells to produce proinflammatory and hematopoietic cytokines," *J. Exp. Med.*, 183:2593–2603, 1996.
Fouilhoux et al., "Production of IL–17 and its regulation in rheumatoid synovium," *American College of Rheumatology (ACR) meeting*, Poster 1447, 1997.
Joosten et al., "IL–1αβ blockade prevents cartilage and bone destruction in murine type II collagen–induced arthritis, whereas TNF–α blockade only ameliorates joint inflammation," *J. Immunol.*, 163:5049–5055, 1999.
Jovanovic et al., "Stimulation of 92–kd gelatinase (matrix metalloproteinase 9) production by interleukin–17 in human monocyte/macrophages," *Arthritis Rheum.*, 43(5):1134–1144, 2000.

(List continued on next page.)

*Primary Examiner*—Janet Andres
(74) *Attorney, Agent, or Firm*—Janis E. Henry; James E. Klaniecki

(57) ABSTRACT

A method of treating a mammal afflicted with rheumatoid arthritis by administering to the mammal an antibody that binds IL-17R is disclosed.

9 Claims, No Drawings

OTHER PUBLICATIONS

Jovanovic, D. et al., "IL–17 stimulates the production and expression of proinflammatory cytokines, IL–β and TNF–α, by human macrophages," *J. of Immunol., 160*:3513–3521, 1998.

Jovanovic, D. et al., "IL–17 stimulates the secretion of proinflammatory cytokines by human macrphages," *American College of Rheumatology (ACR)* meeting, Poster 1446, Nov. 1997.

Kotake, S., "IL–17 in synovial fluids from patients with rheumatoid arthritis is a potent stimulator of osteoclastogenesis," *J. Clin. Invest., 103*(9):1345–1352, 1999.

Lotz et al., IL–17 promotes cartilage degradation, *Arthritis and Rheumatism, 39 supp.*(9):S120, No. 559, 1996.

Spriggs, M. K., "Interleukin–17 and its receptor," *J. Clin. Immunol., 17*(5):366–369, 1997.

Yao, Z. et al., "Molecular characterization of the human inteleukin (IL)–17 receptor," *Cytokine, 9*(11):794–800, 1997.

Yao et al., "Herpesvirus saimiri encodes a new cytokine, IL–17, which binds to a novel cytokine receptor," *Immunity 3*:811–821, 1995.

Yao et al., "Complete nucleotide sequence of the mouse CTLA8 gene," *Gene, 168*:223–225 1996.

Yao et al., "Human IL–17: A novel cytokine derived from T cells," *J. Immunol., 155*5483–5486, 1995.

* cited by examiner

SEQUENCE LISTING

```
<160> NUMBER OF SEQ ID NOS: 4

<210> SEQ ID NO 1
<211> LENGTH: 866
<212> TYPE: PRT
<213> ORGANISM: Homo sapiens

<400> SEQUENCE: 1

Met Gly Ala Ala Arg Ser Pro Pro Ser Ala Val Pro Gly Pro Leu Leu
1               5                   10                  15

Gly Leu Leu Leu Leu Leu Leu Gly Val Leu Ala Pro Gly Gly Ala Ser
                20                  25                  30

Leu Arg Leu Leu Asp His Arg Ala Leu Val Cys Ser Gln Pro Gly Leu
            35                  40                  45

Asn Cys Thr Val Lys Asn Ser Thr Cys Leu Asp Asp Ser Trp Ile His
        50                  55                  60

Pro Arg Asn Leu Thr Pro Ser Ser Pro Lys Asp Leu Gln Ile Gln Leu
65                  70                  75                  80
```

-continued

```
His Phe Ala His Thr Gln Gln Gly Asp Leu Phe Pro Val Ala His Ile
                85                  90                  95
Glu Trp Thr Leu Gln Thr Asp Ala Ser Ile Leu Tyr Leu Glu Gly Ala
                100                 105                 110
Glu Leu Ser Val Leu Gln Leu Asn Thr Asn Glu Arg Leu Cys Val Arg
                115                 120                 125
Phe Glu Phe Leu Ser Lys Leu Arg His His Arg Arg Trp Arg Phe
    130                 135                 140
Thr Phe Ser His Phe Val Val Asp Pro Asp Gln Glu Tyr Glu Val Thr
145                 150                 155                 160
Val His His Leu Pro Lys Pro Ile Pro Asp Gly Asp Pro Asn His Gln
                165                 170                 175
Ser Lys Asn Phe Leu Val Pro Asp Cys Glu His Ala Arg Met Lys Val
                180                 185                 190
Thr Thr Pro Cys Met Ser Ser Gly Ser Leu Trp Asp Pro Asn Ile Thr
                195                 200                 205
Val Glu Thr Leu Glu Ala His Gln Leu Arg Val Ser Phe Thr Leu Trp
                210                 215                 220
Asn Glu Ser Thr His Tyr Gln Ile Leu Leu Thr Ser Phe Pro His Met
225                 230                 235                 240
Glu Asn His Ser Cys Phe Glu His Met His His Ile Pro Ala Pro Arg
                245                 250                 255
Pro Glu Glu Phe His Gln Arg Ser Asn Val Thr Leu Thr Leu Arg Asn
                260                 265                 270
Leu Lys Gly Cys Cys Arg His Gln Val Gln Ile Gln Pro Phe Phe Ser
                275                 280                 285
Ser Cys Leu Asn Asp Cys Leu Arg His Ser Ala Thr Val Ser Cys Pro
                290                 295                 300
Glu Met Pro Asp Thr Pro Glu Pro Ile Pro Asp Tyr Met Pro Leu Trp
305                 310                 315                 320
Val Tyr Trp Phe Ile Thr Gly Ile Ser Ile Leu Leu Val Gly Ser Val
                325                 330                 335
Ile Leu Leu Ile Val Cys Met Thr Trp Arg Leu Ala Gly Pro Gly Ser
                340                 345                 350
Glu Lys Tyr Ser Asp Asp Thr Lys Tyr Thr Asp Gly Leu Pro Ala Ala
                355                 360                 365
Asp Leu Ile Pro Pro Pro Leu Lys Pro Arg Lys Val Trp Ile Ile Tyr
    370                 375                 380
Ser Ala Asp His Pro Leu Tyr Val Asp Val Val Leu Lys Phe Ala Gln
385                 390                 395                 400
Phe Leu Leu Thr Ala Cys Gly Thr Glu Val Ala Leu Asp Leu Leu Glu
                405                 410                 415
Glu Gln Ala Ile Ser Glu Ala Gly Val Met Thr Trp Val Gly Arg Gln
                420                 425                 430
Lys Gln Glu Met Val Glu Ser Asn Ser Lys Ile Ile Val Leu Cys Ser
                435                 440                 445
Arg Gly Thr Arg Ala Lys Trp Gln Ala Leu Leu Gly Arg Gly Ala Pro
                450                 455                 460
Val Arg Leu Arg Cys Asp His Gly Lys Pro Val Gly Asp Leu Phe Thr
465                 470                 475                 480
Ala Ala Met Asn Met Ile Leu Pro Asp Phe Lys Arg Pro Ala Cys Phe
                485                 490                 495
Gly Thr Tyr Val Val Cys Tyr Phe Ser Glu Val Ser Cys Asp Gly Asp
```

|     |     |     |     |     | 500 |     |     |     |     | 505 |     |     |     |     | 510 |     |     |
| --- | --- | --- | --- | --- | --- | --- | --- | --- | --- | --- | --- | --- | --- | --- | --- | --- | --- |
| Val | Pro | Asp | Leu | Phe | Gly | Ala | Ala | Pro | Arg | Tyr | Pro | Leu | Met | Asp | Arg |
|     |     | 515 |     |     |     |     | 520 |     |     |     |     | 525 |     |     |     |
| Phe | Glu | Glu | Val | Tyr | Phe | Arg | Ile | Gln | Asp | Leu | Glu | Met | Phe | Gln | Pro |
|     | 530 |     |     |     |     | 535 |     |     |     |     | 540 |     |     |     |     |
| Gly | Arg | Met | His | Arg | Val | Gly | Glu | Leu | Ser | Gly | Asp | Asn | Tyr | Leu | Arg |
| 545 |     |     |     | 550 |     |     |     | 555 |     |     |     | 560 |     |     |     |
| Ser | Pro | Gly | Gly | Arg | Gln | Leu | Arg | Ala | Ala | Leu | Asp | Arg | Phe | Arg | Asp |
|     |     |     | 565 |     |     |     | 570 |     |     |     | 575 |     |     |     |     |
| Trp | Gln | Val | Arg | Cys | Pro | Asp | Trp | Phe | Glu | Cys | Glu | Asn | Leu | Tyr | Ser |
|     |     | 580 |     |     |     |     | 585 |     |     |     |     | 590 |     |     |     |
| Ala | Asp | Asp | Gln | Asp | Ala | Pro | Ser | Leu | Asp | Glu | Glu | Val | Phe | Glu | Glu |
|     | 595 |     |     |     |     | 600 |     |     |     |     | 605 |     |     |     |     |
| Pro | Leu | Leu | Pro | Pro | Gly | Thr | Gly | Ile | Val | Lys | Arg | Ala | Pro | Leu | Val |
| 610 |     |     |     |     | 615 |     |     |     |     | 620 |     |     |     |     |     |
| Arg | Glu | Pro | Gly | Ser | Gln | Ala | Cys | Leu | Ala | Ile | Asp | Pro | Leu | Val | Gly |
| 625 |     |     |     | 630 |     |     |     | 635 |     |     |     | 640 |     |     |     |
| Glu | Glu | Gly | Gly | Ala | Ala | Val | Ala | Lys | Leu | Glu | Pro | His | Leu | Gln | Pro |
|     |     |     | 645 |     |     |     | 650 |     |     |     | 655 |     |     |     |     |
| Arg | Gly | Gln | Pro | Ala | Pro | Gln | Pro | Leu | His | Thr | Leu | Val | Leu | Ala | Ala |
|     |     | 660 |     |     |     |     | 665 |     |     |     |     | 670 |     |     |     |
| Glu | Glu | Gly | Ala | Leu | Val | Ala | Ala | Val | Glu | Pro | Gly | Pro | Leu | Ala | Asp |
|     | 675 |     |     |     |     | 680 |     |     |     |     | 685 |     |     |     |     |
| Gly | Ala | Ala | Val | Arg | Leu | Ala | Leu | Ala | Gly | Glu | Gly | Ala | Cys | Pro |
| 690 |     |     |     |     | 695 |     |     |     |     | 700 |     |     |     |     |     |
| Leu | Leu | Gly | Ser | Pro | Gly | Ala | Gly | Arg | Asn | Ser | Val | Leu | Phe | Leu | Pro |
| 705 |     |     |     | 710 |     |     |     | 715 |     |     |     | 720 |     |     |     |
| Val | Asp | Pro | Glu | Asp | Ser | Pro | Leu | Gly | Ser | Ser | Thr | Pro | Met | Ala | Ser |
|     |     |     | 725 |     |     |     | 730 |     |     |     | 735 |     |     |     |     |
| Pro | Asp | Leu | Leu | Pro | Glu | Asp | Val | Arg | Glu | His | Leu | Glu | Gly | Leu | Met |
|     |     | 740 |     |     |     |     | 745 |     |     |     |     | 750 |     |     |     |
| Leu | Ser | Leu | Phe | Glu | Gln | Ser | Leu | Ser | Cys | Gln | Ala | Gln | Gly | Gly | Cys |
|     | 755 |     |     |     |     | 760 |     |     |     |     | 765 |     |     |     |     |
| Ser | Arg | Pro | Ala | Met | Val | Leu | Thr | Asp | Pro | His | Thr | Pro | Tyr | Glu | Glu |
| 770 |     |     |     | 775 |     |     |     |     | 780 |     |     |     |     |     |     |
| Glu | Gln | Arg | Gln | Ser | Val | Gln | Ser | Asp | Gln | Gly | Tyr | Ile | Ser | Arg | Ser |
| 785 |     |     |     | 790 |     |     |     | 795 |     |     |     |     |     |     | 800 |
| Ser | Pro | Gln | Pro | Pro | Glu | Gly | Leu | Thr | Glu | Met | Glu | Glu | Glu | Glu | Glu |
|     |     |     | 805 |     |     |     | 810 |     |     |     | 815 |     |     |     |     |
| Glu | Glu | Gln | Asp | Pro | Gly | Lys | Pro | Ala | Leu | Pro | Leu | Ser | Pro | Glu | Asp |
|     |     | 820 |     |     |     |     | 825 |     |     |     | 830 |     |     |     |     |
| Leu | Glu | Ser | Leu | Arg | Ser | Leu | Gln | Arg | Gln | Leu | Leu | Phe | Arg | Gln | Leu |
|     |     | 835 |     |     |     |     | 840 |     |     |     | 845 |     |     |     |     |
| Gln | Lys | Asn | Ser | Gly | Trp | Asp | Thr | Met | Gly | Ser | Glu | Ser | Glu | Gly | Pro |
|     | 850 |     |     |     |     | 855 |     |     |     |     | 860 |     |     |     |     |
| Ser | Ala |
| 865 |     |

<210> SEQ ID NO 2
<211> LENGTH: 212
<212> TYPE: PRT
<213> ORGANISM: Homo sapiens

<400> SEQUENCE: 2

-continued

```
Arg Ser Cys Asp Lys Thr His Thr Cys Pro Pro Cys Pro Ala Pro Glu
1               5                   10                  15

Leu Leu Gly Gly Pro Ser Val Phe Leu Phe Pro Pro Lys Pro Lys Asp
                20                  25                  30

Thr Leu Met Ile Ser Arg Thr Pro Glu Val Thr Cys Val Val Val Asp
            35                  40                  45

Val Ser His Glu Asp Pro Glu Val Lys Phe Asn Trp Tyr Val Asp Gly
    50                  55                  60

Val Glu Val His Asn Ala Lys Thr Lys Pro Arg Glu Glu Gln Tyr Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Ala Leu Pro
                100                 105                 110

Ala Pro Ile Glu Lys Thr Ile Ser Lys Ala Lys Gly Gln Pro Arg Glu
            115                 120                 125

Pro Gln Val Tyr Thr Leu Pro Pro Ser Arg Asp Glu Leu Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Lys
                180                 185                 190

Leu Thr Val Asp Lys Ser Arg Trp Gln Gln Gly Asn Val Phe Ser Cys
            195                 200                 205

Ser Val Met His
        210

<210> SEQ ID NO 3
<211> LENGTH: 31
<212> TYPE: PRT
<213> ORGANISM: Homo sapien

<400> SEQUENCE: 3

Lys Gln Ile Glu Asp Lys Ile Glu Glu Ile Leu Ser Lys Ile Tyr His
1               5                   10                  15

Ile Glu Asn Glu Ile Ala Arg Ile Lys Lys Leu Ile Gly Glu Arg
                20                  25                  30

<210> SEQ ID NO 4
<211> LENGTH: 31
<212> TYPE: PRT
<213> ORGANISM: Homo sapiens

<400> SEQUENCE: 4

Lys Gln Leu Glu Asp Lys Leu Glu Glu Leu Leu Ser Lys Leu Tyr His
1               5                   10                  15

Leu Glu Asn Glu Leu Ala Arg Leu Lys Lys Leu Leu Gly Glu Arg
                20                  25                  30
```

METHODS FOR TREATING RHEUMATOID ARTHRITIS USING IL-17 ANTAGONISTS

This application claims the benefit under U.S.C. 119(e) of U.S. provisional application Ser. No. 60/241,230, filed Oct. 18, 2000. All of which is incorporated by reference herein.

BACKGROUND OF THE INVENTION

1. Field of the Invention

The invention pertains to methods for treating certain diseases and disorders associated with inflammatory and immunoregulatory responses. More particularly, the present invention involves treating rheumatoid arthritis by administering an IL-17 inhibitor or IL-17 antagonist, in particular IL-17 receptor, to an individual afflicted with such rheumatoid arthritis.

2. Description of Related Art

Cytokines are hormone-like molecules that regulate various aspects of an immune or inflammatory response. Cytokines exert their effects by specifically binding receptors present on cells, and transducing a signal to the cells. Rouvier et al. (J. Immunol. 150:5445; 1993) reported a novel cDNA which they termed CTLA-8; cloning of the human homolog led to the identification of this family of molecules as Interleukin-17 (IL-17; Yao et al., Immunity 3:811; 1995). IL-17 is a cytokine produced by activated T cells that stimulates the secretion of various proinflammatory molecules, including tumor necrosis factor $\alpha$ (TNF-$\alpha$), Interleukin-1 $\beta$ (IL-1$\beta$) and prostaglandin $E_2$ ($PGE_2$) from macrophages (Jovanovic et al., J. Immunol. 160:3513; 1998).

TNF-$\alpha$ and IL-1 are believed to play a role in the inflammation and bone destruction that occurs in rheumatoid arthritis (RA), albeit through different mechanisms (Joosten et al., J. Immunol. 163:5049; 1999). Moreover, elevated levels of IL-17 have been reported to occur in the synovial fluid of RA patients, and may play a role in the bone destruction characteristic of RA (Chabaud et al., Arthritis Rheum. 42:963, 1999; Jovanovic et al., Arthritis Rheum. 43:1134, 2000).

IL-17 acts on cells by binding to a specific receptor, IL-17R, which was isolated as described U.S. Pat. No. 6,072,033, issued Jun. 6, 2000. IL-17R is present on numerous cell types, including synoviocytes and monocytes/macrophages. Although there are numerous agents known in the art that are used in the treatment of RA, there is a need to identify additional molecules that can be used to treat or ameliorate the symptoms of this chronic inflammatory disease.

SUMMARY OF THE INVENTION

The present invention relates to a method of treating a mammal afflicted with a condition that relates to an inflammatory response, in particular, rheumatoid arthritis, by administering an IL-17 antagonist that inhibits IL-17 mediated signaling to a cell via membrane-bound IL-17 receptor. Suitable IL-17 antagonists include soluble IL-17 receptor, antagonistic antibodies that specifically bind IL-17, antagonistic antibodies to IL-17 receptor and combinations thereof.

Provided herein are methods for treating medical disorders associated with IL-17 mediated inflammatory reactions or IL-17 mediated immunoregulatory reactions. The methods of the present invention include administering an IL-17 antagonist, or IL-1 inhibitor, that inhibits IL-17 inflammatory or immunoregulatory signaling, to an individual afflicted with an inflammatory or immunoregulatory disease mediated by IL-17. More particularly, the present invention involves administering an IL-17 antagonist such as IL-17 receptor, to an individual inflicted with rheumatoid arthritis, for a period of time sufficient to induce a sustained improvement in the patient's condition.

DETAILED DESCRIPTION OF THE INVENTION

The present invention provides methods for treating an individual including a human, who is suffering from a medical disorder that is associated with IL-17 mediated inflammatory reactions or IL-1 mediated immunoregulatory reactions. For purposes of this disclosure, the terms "illness," "disease," "medical condition" or "abnormal condition" are used interchangeably with the term "medical disorder."

The subject methods involve administering to the patient an IL-17 antagonist or IL-17 inhibitor that is capable of reducing the effective amount of endogenous biologically active IL-17, by preventing the binding of IL-17 to its receptor. Such antagonists include receptor-binding peptide fragments of IL-17, antibodies directed against IL-17 (antibodies that bind IL-17 and inhibit binding thereof to IL-17 receptor), antibodies directed against IL-17 receptor (antibodies that bind IL-17 receptor and inhibit receptor binding of IL-17 without themselves transducing a signal via IL-17 receptor), soluble forms of IL-17 receptor as discussed herein, molecules that bind IL-17 or IL-17 receptor and inhibit the interaction thereof and polypeptides comprising all or portions of receptors for IL-17 or modified variants thereof, including genetically-modified muteins, multimeric forms and sustained-release formulations thereof. Particular antagonists are soluble forms of IL-17 receptor. Other particular IL-17 antagonists encompass chimeric proteins that include portions of both an antibody molecule and an IL-17 antagonist molecule, particularly a soluble portion of IL-17 receptor fused to an Fc. Such chimeric molecules may form monomers, dimers or higher order multimers. Preferred methods of the invention utilize IL-17 receptor in a form that binds IL-17 and blocks IL-17 signal transduction, thereby interrupting the proinflammatory and immunoregulatory effects of IL-17.

The characterization, cloning and preparation of IL-17 receptor is described U.S. Pat. No. 6,072,033, issued Jun. 6, 2000, incorporated herein by reference. The amino acid sequence of the human IL-17 receptor (huIL-17 receptor) is shown in SEQ ID NO:1. The huIL-17 receptor has an N-terminal signal peptide with a predicted cleavage site between amino acid 27 and 28. The signal peptide is followed by a 293 amino acid extracellular domain, a 21 amino acid transmembrane domain, and a 525 amino acid cytoplasmic tail. Soluble forms of huIL-17 receptor that are useful in the methods of the present invention include the extracellular domain (residues 1–320 of SEQ ID NO:1 or residues 28–320 which excludes the signal peptide) or a fragment of the extracellular domain that has the properties of antagonizing or preventing binding of IL-17 receptor to IL-17. Other forms of the IL-17 receptor that are useful in the present invention include muteins and variations that are at least 70% or at least 90% homologous to the native IL-17 receptor of SEQ ID NO:1 and as described in U.S. Pat. No. 6,072,033.

Other derivatives of the IL-17 receptor protein and homologs thereof that are useful in the practice of this inventive method include covalent or aggregative conjugates of the protein or its fragments with other proteins or polypeptides, such as by synthesis in recombinant culture as N-terminal or C-terminal fusions. For example, the conjugated peptide may be a signal (or leader) polypeptide sequence at the N-terminal region of the protein which co-translationally or post-transitionally directs transfer of the protein from its site of synthesis to its site of function inside or outside of the cell membrane or wall (e.g., the yeast a-factor leader).

Suitable forms of IL-17 inhibitors include chimeric proteins which include a second polypeptide that may promote the spontaneous formation by the chimeric protein of a dimer, trimer or higher order multimer that is capable of binding IL-17 and preventing it from binding to a cell-bound receptor that promotes IL-17 signaling and inhibits or reduces the effects of inflammation and symptoms of rheumatoid arthritis. Chimeric proteins used as antagonists may be proteins that contain portions of an antibody molecule and a soluble IL-17 receptor. Suitable fusion proteins include a IL-17 receptor polypeptide, e.g. the extracellular domain, or an IL-17 antagonistic fragment of the extracellular domain, linked to an immunoglobulin Fc region. Fragments of an Fc region may also be used, as well as Fc muteins that exhibit decreased affinity for Fc receptors. A preferred Fc region is shown in SEQ ID NO:2. Depending on the portion of the Fc region used, a fusion protein may be expressed as a dimer, through formation of interchain disulfide bonds. If the fusion proteins are made with both heavy and light chains of an antibody, it is possible to form a protein oligomer with as many as four IL-17 receptor regions.

Oligomeric forms of IL-17 inhibitors suitable for use in the present invention also include an IL-17 receptor, the extracellular domain of an IL-17 receptor, or an IL-17 inhibiting fragment of the extracellular domain associated with a zipper domain, such as zipper proteins described in U.S. Pat. No. 5,716,805, the disclosure of which is incorporated by reference herein. Other Examples of zipper domains are those found in the yeast transcription factor GCN4 and a heat-stable DNA-binding protein found in rat liver (C/EBP; Landschulz et al., *Science* 243:1681, 1989), the nuclear transforming proteins, fos and jun, which preferentially form a heterodimer (O'Shea et al., *Science* 245:646, 1989; Turner and Tjian, *Science* 243:1689, 1989), and the gene product of the murine proto-oncogene, c-myc (Landschulz et al., *Science* 240:1759, 1988). The fusogenic proteins of several different viruses, including paramyxovirus, coronavirus, measles virus and many retroviruses, also possess leucine zipper domains (Buckland and Wild, *Nature* 338:547, 1989; Britton, *Nature* 353:394, 1991; Delwart and Mosialos, *AIDS Research and Human Retroviruses* 6:703, 1990). Examples of preferred zipper domains are those of SEQ ID NO:3 and SEQ ID NO:4.

Other types of protein-based therapeutics are antibodies that specifically recognize one or more epitopes of IL-17, or epitopes of conserved variants of IL-17, or peptide fragments of the IL-17 polypeptide that competitively inhibit IL-17 activity. Antibodies to IL-17 can most conveniently be raised to a recombinantly produced form of the protein. Or, antibodies that specifically recognize a component of the IL-17 receptor and that prevent signaling through the receptor by IL-17 can be used to inhibit IL-17 activity. IL-17 antagonists that are antibodies include but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Thus, such antibodies can, therefore, be utilized as part of inflammatory disorder treatment methods.

For the production of antibodies, various host animals can be immunized by injection with the IL-17 polypeptide, truncated IL-17 polypeptides, a component of the IL-17 receptor (e.g., the IL-17 extracellular region), a truncated version of a component of the IL-17 receptor, and functional equivalents and mutants thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum. Alternatively, libraries of antibody fragments can be screened and used to develop human antibodies through recombinant techniques. Such libraries are commercially available from, for example, Cambridge Antibody Technology (Melbourne, UK), and Morphosys (Munich, DE).

Monoclonal antibodies, which are homogeneous populations of antibodies to a particular antigen, can be obtained by any technique that provides for the production of antibody molecules by continuous cell lines in culture. These include, but are not limited to, the hybridoma technique of Kohler and Milstein, (U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb may be cultivated in vitro or in vivo. Or, the antibody genes can be cloned and optionally otherwise altered, and expressed in another cell line approved for recombinant production of protein pharmaceuticals such as, for example, CHO cells.

In addition, techniques developed for the production of "chimeric antibodies" (Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a porcine mAb and a human immunoglobulin constant region.

Preferably, for use in humans, the antibodies are human or humanized; techniques for creating such human or humanized antibodies are also well known and are commercially available from, for example, Protein Design Labs, Inc. (Fremont, Calif.), Medarex Inc. (Princeton, N.J.) and Abgennix Inc. (Fremont, Calif.).

Techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can also be adapted to produce single chain antibodies against IL-17 gene products and IL-17 receptor gene products. Single chain antibodies are formed by linking the heavy and light chain fragments of the Fv region via an amino acid bridge, resulting in a single chain polypeptide.

Antibody fragments that recognize specific epitopes can be generated by known techniques. For example, such fragments include but are not limited to: the F(ab')$_2$ fragments which can be produced by pepsin digestion of the antibody molecule and the Fab fragments which can be generated by reducing the disulfide bridges of the (ab')$_2$ fragments. Alternatively, Fab expression libraries can be constructed (Huse et al., 1989, Science, 246:1275–1281) to allow rapid and easy identification of monoclonal Fab fragments with the desired this invention additionally provides for the use of soluble forms of IL-17 receptor, including the extracellular domain and suitable fragments thereof in the manufacture of a medicament for the prevention or treatment of rheumatoid arthritis. This invention additionally provides for the use of DNA encoding human IL-17 receptor, as described in U.S. Pat. No. 6,072,033, in the manufacture of soluble IL-17 receptor for use in the manufacture of a medicament for the treatment of rheumatoid arthritis.

In one preferred embodiment of the invention, sustained-release forms of soluble IL-17 receptor, or other IL-17 inhibitors described herein, are used. Sustained-release forms suitable for use in the disclosed methods include, but are not limited to, IL-17 receptor or other IL-17 inhibitor, that is encapsulated in a slowly-dissolving biocompatible polymer, admixed with such a polymer, and or encased in a biocompatible semi-permeable implant. In addition, the soluble IL-17 receptor or may be conjugated with polyethylene glycol (pegylated) to prolong its serum half-life or to enhance protein delivery. Soluble forms of IL-17 receptor, including monomers, fusion proteins (also called "chimeric proteins), dimers, trimers or higher order multimers, are useful in formulating IL-17 antagonists for treating rheumatoid arthritis. Similarly, antibodies that antagonize the IL-17/IL-17R interaction and signaling pathway are useful antagonists for treating rheumatoid arthritis.

To treat rheumatoid arthritis, a molecule comprising an IL-17 binding soluble IL-17 receptor, or antibody as described herein, is administered to the patient in an amount and for a time sufficient to induce a sustained improvement in at least one indicator that reflects the severity of the rheumatoid arthritis. An improvement is considered "sustained" if the patient exhibits, or experiences as self-assessed, the improvement on at least two occasions separated by one to four weeks. The degree of improvement is determined based on signs or symptoms, and may also employ questionnaires that are administered to the patient, such as quality-of-life questionnaires.

Various indicators that reflect the extent of the patient's rheumatoid arthritis may be assessed for determining whether the amount and time of the treatment is sufficient. The baseline value for the chosen indicator or indicators is established by examination of the patient, or the patient's own self assessment, prior to administration of the first dose of the soluble IL-17 receptor, or antagonistic antibody, as described above. Preferably, the baseline examination is done within about 60 days of administering the first dose.

Improvement is induced by repeatedly administering a dose of soluble IL-17 receptor or other suitable IL-17 receptor derivative, or antibody, as described herein, until the patient manifests an improvement over baseline for the chosen indicator or indicators. The degree of improvement is obtained by repeatedly administering the medicament over a period of at least a month or more, e.g., for one, two, or three months or longer, or indefinitely.

Any efficacious route of administration may be used to therapeutically administer IL-17 receptor or antibody, as described herein. If injected, a IL-17 inhibitor can be administered, for example, via intra-articular, intravenous, intramuscular, intralesional, intraperitoneal or subcutaneous routes by bolus injection or by continuous infusion.

Other suitable means of administration include sustained release from implants, aerosol inhalation, eyedrops, oral preparations, including pills, syrups, lozenges or chewing gum, and topical preparations such as lotions, gels, sprays, ointments or other suitable techniques. Administration by inhalation is particularly beneficial when treating diseases associated with pulmonary disorders. Alternatively, IL-17 inhibitor polypeptides, such as a soluble IL-17 receptor, may be administered by implanting cultured cells that express the protein; for example, by implanting cells that express a soluble IL-17 receptor. In one embodiment, the patient's own cells are induced to produce by transfection in vivo or ex vivo with a DNA that encodes an IL-17 inhibitor, and particularly soluble IL-17 receptor. This DNA can be introduced into the patient's cells, for example, by injecting naked DNA or liposome-encapsulated DNA that encodes soluble IL-17 receptor, or by other means of transfection. When soluble IL-17 receptor is administered in combination with one or more other biologically active compounds, these may be administered by the same or by different routes, and may be administered simultaneously, separately or sequentially.

Soluble IL-17 receptor or other antagonists of IL-17 preferably are administered in the form of a physiologically acceptable composition comprising purified recombinant protein in conjunction with physiologically acceptable carriers, excipients or diluents. Such carriers are nontoxic to recipients at the dosages and concentrations employed. Ordinarily, preparing such compositions entails combining the IL-17 antagonist with buffers, antioxidants such as ascorbic acid, low molecular weight polypeptides (such as those having fewer than 10 amino acids), proteins, amino acids, carbohydrates such as glucose, sucrose or dextrins, chelating agents such as EDTA, glutathione and other stabilizers and excipients. Neutral buffered saline or saline mixed with conspecific serum albumin are exemplary appropriate diluents. The IL-17 receptor or antagonistic antibody, preferably is formulated as a lyophilizate using appropriate excipient solutions (e.g., sucrose) as diluents. Appropriate dosages can be determined in standard dosing trials, and may vary according to the chosen route of administration. In accordance with appropriate industry standards, preservatives may also be added, such as benzyl alcohol. The amount and frequency of administration will depend, of course, on such factors as the nature and severity of the indication being treated, the desired response, the age and condition of the patient, and so forth.

In one embodiment of the invention, the IL-17 inhibitor is administered one time per week to treat rheumatoid arthritis, in another embodiment is administered at least two times per week, and in another embodiment is administered at least once per day. An adult patient is a person who is 18 years of age or older. If injected, the effective amount, per adult dose, ranges from 1–200 mg/m$^2$, or from 1–40 mg/m$^2$ or about 5–25 mg/m$^2$. Alternatively, a flat dose may be administered, whose amount may range from 2–400 mg/dose, 2–100 mg/dose or from about 10–80 mg/dose. If the dose is to be administered more than one time per week, an exemplary dose range is the same as the foregoing described dose ranges or lower. Preferably, the IL-17 inhibitor is administered two or more times per week at a per dose range of 25–100 mg/dose. In one embodiment of the invention, the various indications described below are treated by administering a preparation acceptable for injection containing IL-17 inhibitor at 80–100 mg/dose, or alternatively, containing 80 mg per dose. The dose is administered repeatedly. If a route of administration other than injection is used, the dose is appropriately adjusted in accord with standard medical practices. For example, if the route of administration is inhalation, dosing may be one to seven times per week at dose ranges from 10 mg/dose to 50 mg per dose.

In many instances, an improvement in a patient's condition will be obtained by injecting a dose of up to about 100 mg of IL-17 inhibitor one to three times per week over a period of at least three weeks, though treatment for longer periods may be necessary to induce the desired degree of improvement.

For pediatric patients (age 4–17), a suitable regimen involves the subcutaneous injection of 0.4 mg/kg to 5 mg/kg of IL-17 inhibitor, administered by subcutaneous injection one or more times per week.

The invention further includes the administration of an IL-17 inhibitor concurrently with one or more other drugs that are administered to the same patient, each drug being administered according to a regimen suitable for that medicament. This encompasses pre-treatment, simultaneous treatment, sequential treatment and alternating regimens. Examples of such drugs include but are not limited to analgesics, corticosteroids, antagonists of inflammatory cytokines, DMARDs, including methotrexate, and non-steroidal anti-inflammatories. Additionally, IL-17 inhibitors described herein, may be combined with each other or combined with other molecules that reduce endogenous IL-17 levels.

In one preferred embodiment of the invention, methods for treating rheumatoid arthritis include administering soluble IL-17 receptor or other IL-17 inhibitor described herein, in combination with one or more additional cytokines or cytokine inhibitors. For example, an IL-17 inhibitor may be administered in a composition with agents that inhibit the interaction of inflammatory cytokines with their receptors. Suitable agents that may be utilized in combination with IL-17 inhibitors, but are not limited to, IL-1 inhibitors, such as type II IL-1 receptor, including IL-1 binding fragments of type II IL-1 receptor, disclosed in U.S. Pat. No. 5,350,683; IL-1 binding and IL-1 inhibitory fragments of type I IL-1 receptor; IL-1 receptor antagonist, IL-1 beta converting enzyme (ICE) inhibitors, antibodies to IL-1, including IL-1 alpha and IL-1 beta and other IL-1 family members, and therapeutics known as IL-1 traps and antagonistic type I IL-1 receptor antibodies; TNF inhibitors such as antagonistic TNF antibodies; soluble TNF receptors p55 and p75, particularly ENBREL; IL-18 inhibitors including IL-18 binding protein disclosed in WO 0012555; inhibitory forms of IL-18 receptors, disclosed in WO 99/37772; antagonist IL-18 antibodies, and antagonistic IL-18 receptor antibodies; CD30-ligand inhibitors; and, CD4 inhibitors.

Specific IL-1 inhibitors include forms of IL-1ra described in U.S. Pat. No. 5,075,222 and modified forms and variants including those described in U.S. Pat. No. 5,922,573, WO 91/17184, WO 92 16221, and WO 96 09323, all of which are incorporated herein by reference. IL-1 beta converting enzyme (ICE) inhibitors include peptidyl and small molecule ICE inhibitors including those described in PCT patent applications WO 91/15577; WO 93/05071; WO 93/09135; WO 93/14777 and WO 93/16710; and European patent application 0 547 699. Non-peptidyl compounds include those described in PCT patent application WO 95/26958, U.S. Pat. No. 5,552,400, U.S. Pat. No. 6,121,266, Dolle et al., J. Med. Chem., 39, pp. 2438–2440 (1996). Additional ICE inhibitors are described in U.S. Pat. Nos. 6,162,790, 6,204,261, 6,136,787, 6,103,711, 6,025,147, 6,008,217, 5,973,111, 5,874,424, 5,847,135, 5,843,904, 5,756,466, 5,656,627, 5,716,929.

Further, suitable IL-1 antagonists encompass chimeric proteins that include portions of both an antibody molecule and an IL-1 antagonist molecule. Such chimeric molecules may form monomers, dimers or higher order multimers. Other suitable IL-1 antagonists include peptides derived from IL-1 that are capable of binding competitively to the IL-1 signaling receptor, IL-1 R type I.

Additional inhibitors used in combination with IL-17 receptor include those that antagonize TGFβ, IFNγ, IL-6 or IL-8. The cytokine inhibitors may be administered as separate compositions, or together with IL-17 receptor, and the cytokine inhibitors may be administered by the same or different routes.

Where the compounds are used together with one or more other components, the compound and the one or more other components may be administered simultaneously, separately or sequentially (usually in pharmaceutical format).

It is understood that the response by individual patients to the aforementioned medications or combination therapies may vary, and the most efficacious combination of drugs for each patient will be determined by the treating physician or physicians.

The following examples are offered by way of illustration, and not by way of limitation. Those skilled in the art will recognize that variations of the invention embodied in the examples can be made, especially in light of the teachings of the various references cited herein, the disclosures of which are incorporated by reference herein.

EXAMPLE 1

This example describes a construct for expression of an IL-17R/Fc fusion protein. Construction of the IL-17 receptor DNA is described in U.S. Pat. No. 6,072,033, issued Jun. 6, 2000. Briefly, a soluble form of IL-17 receptor fused to the Fc region of human IgG1 was constructed in the mammalian expression vector pDC409 by utilizing a 980 bp DNA fragment (nucleotides encoding the amino acid sequence of residues 1 to 322 of IL-17 receptor as shown in SEQ ID NO:1) amplified from IL-17 receptor cDNA in a three way ligation with a DNA fragment encoding human IgG1 Fc (SEQ ID NO:3) and the plasmid pDC409 (described U.S. Ser. No. 08/235,397).

The IL-17 receptor/Fc expression plasmids were transfected into mammalian cells (for example, CV-1/EBNA cells), and supernatants collected. Following the collection, the IL-17 receptor/Fc fusion proteins were purified on a protein A sepharose column (Pharmacia, Uppsala, Sweden) as described below. Protein concentration was determined by an enzyme-linked immunoadsorbent assay specific for the IgG Fc domain and by BCA analysis (Pharmacia); purity was confirmed by SDS-polyacrylamide gel electrophoresis analysis followed by silver stain of the gel.

EXAMPLE 2

This example describes purification of IL-17 receptor fusion proteins. IL-17 receptor/Fc fusion protein was purified by conventional methods using Protein A or Protein G chromatography. Approximately one liter of culture supernatant containing IL-17 receptor/Fc fusion protein was purified by filtering mammalian cell supernatants (e.g., in a 0.45 m filter) and applying filtrate to a protein A/G antibody affinity column (Schleicher and Schuell, Keene, N.H.) at 4° C. at a flow rate of 80 ml/hr for a 1.5 cm×12.0 cm column. The column was washed with 0.5 M NaCl in PBS until free protein was not detected in the wash buffer. Finally, the column was washed with PBS. Bound fusion protein was eluted from the column with 25 mM citrate buffer, pH 2.8, and brought to pH 7 with 500 mM Hepes buffer, pH 9.1.

EXAMPLE 3

This example describes results obtained using IL-17 receptor in a murine model of rheumatoid arthritis. Mice (male DBA/1 mice five to eight weeks old) were immunized intradermally at the base of the tail with 100 μg type II collagen (CII) in complete Freund's adjuvant ((IFA). Twenty-one days later, the mice were boosted with 200 μg CII in incomplete Freund's adjuvant (IFA) intradermally at the base of the tail. Signs of clinical arthritis begin to appear in the mice three to five days after the booster.

Mice were evaluated for signs of clinical score and disease incidence three times weekly, beginning at the time of the booster. Disease severity was evaluated using an established arthritis index system. Each paw was assigned a clinical score based on the index. Paw scores for each animal were combined to determine a total cumulative score. The arthritis index used was: 0=normal appearance; 1=erythema/edema in 1–2 digits; 2=erythema/edema in more than two digits, or mild swelling in ankle/wrist joint; 3=erythema/edema in entire paw; 4=massive erythema/edema of entire paw extending into proximal joints, ankylosis, loss of function.

At the time of the booster, mice (15–20 mice per group) were injected intraperitoneally with either 150 μg rat IgG, 1 μg TNF receptor/Fc, 150 μg IL-17 receptor/Fc as prepared in Examples 1 and 2, or a combination of 1 μg TNF receptor/Fc and 150 μg IL-17 receptor/Fc. The treatment regimen was repeated daily for fourteen days. The mice were evaluated for clinical score and disease incidence three times weekly.

The average final score for each group is shown in Table 1.

TABLE 1

Decrease of Arthritis Symptoms in Mice Given TNF receptor/Fc and/or IL-17 receptor/Fc

| Group: | Treatment: | Average Final Score: |
|---|---|---|
| Group 1 | Rat IgG | 8.4 |
| Group 2 | TNF receptor/Fc | 5.7 |
| Group 3 | IL-17 receptor/Fc | 5.1 |
| Group 4 | TNF receptor/Fc plus IL-17 receptor/Fc | 1.7 |

A second set of experiment using substantially the same parameters was carried out. The average final score for each group is shown in Table 2:

TABLE 2

Decrease of Arthritis Symptoms in Mice Given TNF receptor/Fc and IL-17 receptor/Fc.

| Group: | Treatment: | Average Final Score: |
|---|---|---|
| Group 1 | Rat IgG | 9.2 |
| Group 2 | TNF receptor/Fc | 5.9 |
| Group 3 | IL-17 receptor/Fc | 3.9 |
| Group 4 | TNF receptor/Fc plus IL-17 receptor/Fc | 5.0 |

These results indicate that IL-17 receptor ameliorates the symptoms of arthritis in an animal model of rheumatoid arthritis. Moreover, IL-17 receptor may be used in combination with TNF receptor (or other inhibitors of inflammation) to reduce the severity of clinical arthritis.

What is claimed is:

1. A method of treating an individual afflicted with rheumatoid arthritis, the method comprising administering to the individual an IL-17 receptor antibody, wherein the IL-17 receptor antibody inhibits IL-17 receptor signal transduction.

2. The method of claim 1, further comprising administering one or more therapeutics selected from the group consisting of TNF antagonist, IL-1 antagonist and DMARD.

3. The method of claim 2 wherein the TNF antagonist is selected from the group consisting of TNF antibodies, soluble TNF receptor p75, and soluble TNF receptor p55.

4. The method of claim 2 wherein the IL-1 antagonist is selected from the group consisting of soluble IL-1 receptor type II, IL-1R type I antibody, IL-1 receptor antagonist, and fusion protein comprising soluble IL-1 receptor type I, and soluble IL-1 receptor accessory protein.

5. The method of claim 2 wherein the DMARD is methotrexate.

6. A method of treating an individual afflicted with rheumatoid arthritis, the method comprising administering to the individual a therapeutic comprising an antibody that binds a polypeptide selected from the group consisting of:
   (a) a polypeptide having amino acids 33 through 320 of SEQ ID NO:1;
   (b) a polypeptide having amino acids 28 through 320 of SEQ ID NO:1;
   (c) a polypeptide having amino acids 1–320 of SEQ ID NO:1;
   (d) a polypeptide having amino acids 1–866 of SEQ ID NO:1;
   (e) a polypeptide having amino acids 28–866 of SEQ ID NO:1; and
   (f) a polypeptide having amino acids 33–866 of SEQ ID NO:1.

7. The method according to claim 1, further comprising administering one or more therapeutics selected from the group consisting of a TNF antagonist and an IL-1 antagonist.

8. The method of claim 7 wherein the IL-1 antagonist is selected from the group consisting of soluble IL-1 receptor type II, IL-1R type I antibody, IL-1 receptor antagonist, and fusion protein comprising soluble IL-1 receptor type I and soluble IL-1 receptor accessory protein.

9. The method of claim 7 wherein the TNF antagonist is selected from the group consisting of TNF antibodies, soluble TNF receptor p75, and soluble TNF receptor p55.

* * * * *